(12) United States Patent
Groden et al.

(10) Patent No.: US 10,004,652 B1
(45) Date of Patent: Jun. 26, 2018

(54) SAFETY SYSTEM FOR AERIAL VEHICLES AND METHOD OF OPERATION

(71) Applicant: SkyRyse, Inc., San Francisco, CA (US)

(72) Inventors: Mark Groden, San Francisco, CA (US); Mitch Adler, San Francisco, CA (US)

(73) Assignee: SkyRyse, Inc., San Francisco, CA (US)

( * ) Notice: Subject to any disclaimer, the term of this patent is extended or adjusted under 35 U.S.C. 154(b) by 0 days. days.

(21) Appl. No.: 15/904,082

(22) Filed: Feb. 23, 2018

Related U.S. Application Data

(63) Continuation of application No. 15/661,763, filed on Jul. 27, 2017, which is a continuation of application
(Continued)

(51) Int. Cl.
| | |
|---|---|
| *B64D 47/00* | (2006.01) |
| *A61G 3/00* | (2006.01) |
| *G08G 5/00* | (2006.01) |
| *G07C 5/00* | (2006.01) |
| *B64F 5/60* | (2017.01) |
| *B64D 45/08* | (2006.01) |
| *G05D 1/00* | (2006.01) |
| *B64F 1/18* | (2006.01) |
| *G16H 40/20* | (2018.01) |
| *G06Q 50/30* | (2012.01) |
| *G06Q 10/02* | (2012.01) |
| *G08B 7/06* | (2006.01) |

(Continued)

(52) U.S. Cl.
CPC ............. *A61G 3/001* (2013.01); *B64D 45/08* (2013.01); *B64D 47/00* (2013.01); *B64F 1/18* (2013.01); *B64F 5/60* (2017.01); *G05D 1/0088* (2013.01); *G06Q 10/02* (2013.01); *G06Q 50/30* (2013.01); *G07C 5/008* (2013.01); *G08G 5/003* (2013.01); *G08G 5/0013* (2013.01); *G08G 5/0034* (2013.01); *G08G 5/0056* (2013.01); *G08G 5/0095* (2013.01); *G16H 40/20* (2018.01); *A61G 2220/10* (2013.01); *G06K 9/00771* (2013.01); *G08B 7/06* (2013.01); *G16H 15/00* (2018.01)

(58) Field of Classification Search
CPC ....... A61G 3/001; A61G 2220/10; B64F 5/60; B64F 1/18; B64D 45/08; B64D 17/24; G16H 40/20; G16H 15/00; G05D 1/0088; G06Q 10/02; G06Q 50/30; G06K 9/00771; G07C 5/008; G08G 5/0013; G08G 5/003; G08G 5/0034; G08G 5/0056; G08G 5/0095; G08B 7/06
See application file for complete search history.

(56) References Cited

U.S. PATENT DOCUMENTS

| | | |
|---|---|---|
| 3,455,182 A | 7/1969 | Archibald |
| 4,957,121 A | 9/1990 | Icenogle et al. |

(Continued)

*Primary Examiner* — Behrang Badii
*Assistant Examiner* — Daniel L Greene
(74) *Attorney, Agent, or Firm* — Jeffrey Schox

(57) ABSTRACT

A safety system for an aerial vehicle, preferably including: a ballistic subsystem, preferably including one or more rockets operable to adjust motion of the aerial vehicle and a mounting unit that couples the ballistic subsystem to the aerial vehicle; and/or a deployable parachute subsystem. An aerial vehicle, preferably including a safety system. A method for aerial vehicle operation, preferably including activating a safety system.

20 Claims, 9 Drawing Sheets

Related U.S. Application Data

No. 15/643,205, filed on Jul. 6, 2017, now Pat. No. 9,849,044.

(60) Provisional application No. 62/452,051, filed on Jan. 30, 2017, provisional application No. 62/469,419, filed on Mar. 9, 2017, provisional application No. 62/463,247, filed on Feb. 24, 2017.

(51) Int. Cl.
*G06K 9/00* (2006.01)
*G16H 15/00* (2018.01)

(56) References Cited

U.S. PATENT DOCUMENTS

| | | | |
|---|---|---|---|
| 5,493,309 A | 2/1996 | Bjornholt | |
| 6,776,373 B1* | 8/2004 | Talmage, Jr. | B64D 25/12 244/140 |
| 7,458,544 B1* | 12/2008 | Sarigul-Klijn | B64D 1/12 244/137.3 |
| 8,033,507 B2* | 10/2011 | Fox, Jr. | B64D 17/383 244/151 B |
| 8,948,935 B1 | 2/2015 | Peeters et al. | |
| 8,979,032 B1 | 3/2015 | Hester, Jr. et al. | |
| 9,158,304 B2 | 10/2015 | Fleck | |
| 9,308,970 B1* | 4/2016 | Gefken | B63B 21/48 |
| 9,868,526 B2* | 1/2018 | Yates | B64C 39/024 |
| 2005/0087652 A1 | 4/2005 | Holmboe | |
| 2005/0127238 A1* | 6/2005 | Ballew | B64C 27/10 244/10 |
| 2005/0139363 A1* | 6/2005 | Thomas | A62C 3/025 169/30 |
| 2005/0230555 A1* | 10/2005 | Strong | B64D 1/08 244/152 |
| 2006/0032984 A1* | 2/2006 | Preston | G07F 17/32 244/152 |
| 2006/0208136 A1* | 9/2006 | Cook | B64G 1/005 244/171.3 |
| 2007/0262203 A1* | 11/2007 | Saggio, III | B64D 39/00 244/135 A |
| 2009/0008499 A1* | 1/2009 | Shaw | B64C 27/20 244/17.23 |
| 2010/0213718 A1* | 8/2010 | Kelly | F03D 5/04 290/55 |
| 2011/0009053 A1* | 1/2011 | Anglin, Jr. | H04B 7/2606 455/9 |
| 2012/0011996 A1* | 1/2012 | Glasson | F41H 11/04 89/36.17 |
| 2012/0228432 A1* | 9/2012 | Fox, Jr. | B64D 1/08 244/137.3 |
| 2013/0221159 A1* | 8/2013 | Giannakopoulos | B64C 13/30 244/139 |
| 2014/0067164 A1* | 3/2014 | Papadopoulos | B64G 1/002 701/3 |
| 2015/0203200 A1* | 7/2015 | Bye | B64C 39/024 244/13 |
| 2016/0318615 A1* | 11/2016 | Pick | B64C 39/024 |

* cited by examiner

SAFETY SYSTEM FOR AERIAL VEHICLES AND METHOD OF OPERATION

CROSS-REFERENCE TO RELATED APPLICATIONS

This application is a continuation-in-part of U.S. patent application Ser. No. 15/661,763, filed 27 Jul. 2017, which is a continuation of U.S. patent application Ser. No. 15/643,205, filed on 6 Jul. 2017, which claims the benefit of U.S. Provisional Application Ser. No. 62/452,051, filed on 30 Jan. 2017, and U.S. Provisional Application Ser. No. 62/469,419, filed on 9 Mar. 2017, all of which are incorporated in their entirety by this reference.

This application claims the benefit of U.S. Provisional Application Ser. No. 62/463,247, filed on 24 Feb. 2017, which is incorporated in its entirety by this reference.

TECHNICAL FIELD

This invention relates generally to the field of aerial vehicles and more specifically to a new and useful safety system for aerial vehicles.

BACKGROUND

The inventions described herein relate to systems and methods for increasing the safety of aerial vehicles. In certain configurations, current aerial vehicles can be operated in a manner that trades kinetic energy for potential energy or potential energy for kinetic energy, in order to recover from an unsafe situation or attitude. In one typical scenario, altitude can be traded for airspeed, in order to recover from an emergency that occurs in a slow flight or a stalled configuration.

However, certain states of an aerial vehicle, where the total energy (e.g., kinetic and potential energies) available is below a threshold, can produce scenarios where flight recovery is impossible without damage to the aerial vehicle or to its occupants in the event of an emergency. An example of this is the "dead man's curve" for rotorcraft, where emergencies in low airspeed and low altitude configurations produce an unrecoverable aerial vehicle state.

As such, there is a need in the field of aerial vehicles for a new and useful safety system. The inventions described herein create such a new and useful safety system and method.

DESCRIPTION OF THE EMBODIMENTS

The following description of the embodiments of the invention is not intended to limit the invention to these embodiments, but rather to enable any person skilled in the art to make and use this invention.

1. System.

Figure 1:
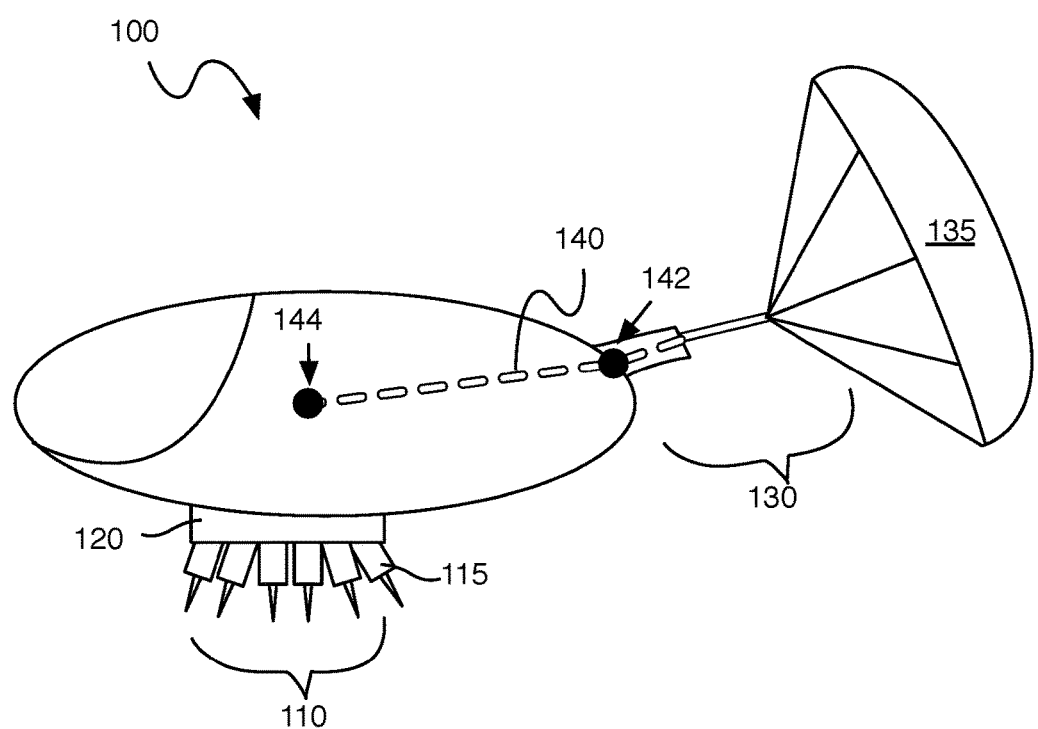
FIG. 1 is a schematic representation of an embodiment of a safety system for an aerial vehicle.

As shown in FIG. 1, an embodiment of a safety system 100 for an aerial vehicle preferably includes: a ballistic subsystem 110 including one or more rockets 115 operable to adjust motion of the aerial vehicle; and a mounting unit 120 that couples the ballistic subsystem to the aerial vehicle. The system 100 can additionally or alternatively include a deployable parachute subsystem 130 coupled to a region of the aerial vehicle and operable to deploy a parachute 135; and a connector 140 coupled to the parachute, to a first anchoring point 142 of the aerial vehicle, and to a second anchoring point 144 separated from the first anchoring point of the aerial vehicle.

The system 100 preferably functions to provide one or more "last-resort" safety mechanisms for an aerial vehicle, implementing one or more of a rocket-based approach and a ballistic parachute approach. In variations, the rocket and ballistic parachute system components can be deployed independently of each other, and can be deployed in parallel, in series, or in any other suitable manner. Additionally or alternatively, the systems described herein can supplement function of safety mechanisms intrinsic to the aerial vehicle. In examples, such safety mechanisms can include autorotation operations for rotorcraft and gliding operations for fixed-wing aircraft. Alternatively, some variations of the system 100 can omit one of the rocket system and the ballistic parachute system.

In some variations, the system 100 can cooperate or coordinate with autonomous or semi-autonomous aerial vehicle systems that provide real-time information regarding the aerial vehicle's orientation, integrity of systems of the aerial vehicle (e.g., power plant integrity, control surface integrity, electrical system integrity, navigation system integrity, etc.), altitude, terrain, nearby obstacles, airspace, environmental conditions (e.g., density altitude, temperature, temperature/dewpoint spread, pressure, daylight, visibility, winds, etc.), and any other suitable information relevant to flight of the aerial vehicle. Such autonomous or semi-autonomous systems can be used to trigger deployment of one or more of the rocket system and the ballistic parachute system, as well as to continue controlling execution and coordination of such systems. Embodiments, variations, and examples of such systems are described in U.S. application Ser. No. 15/661,763, titled "Vehicle System and Method for Providing Services", which is herein incorporated in its entirety by this reference. However, the system 100 can additionally or alternatively cooperate with any other suitable autonomous or semi-autonomous system. Still further, the system 100 can alternatively be used in a non-autonomous manned aerial vehicle (e.g., aircraft carrying a human pilot) or remotely operated aerial vehicle (e.g., a drone).

In embodiments, the aerial vehicle can be a rotorcraft, such that the system 100 components are coupled to one or more portions of the rotorcraft (e.g., the airframe of the rotorcraft, the fuselage of the rotorcraft, etc.). For example, the rotorcraft can include any or all of: an airframe, a rotor rotationally coupled to the airframe about a rotor axis, and/or a power plant (e.g., piston engine, turbine engine, etc.) configured to drive rotation of the rotor (e.g., mechanically coupled to the rotor by a power transmission, such as a driveshaft). The rotorcraft can optionally include multiple rotors, such as tandem rotors (e.g., with rotor axes at a small angle to each other, such as substantially parallel and/or angle less than 1°, 5°, 10°, 15°, 30°, 45°, 1-5°, 5-20°, 20-60°, etc.), or a main rotor and a tail rotor (e.g., with a tail rotor axis substantially perpendicular the main rotor axis). However, the rotorcraft can additionally or alternatively include any other suitable rotors and/or other elements in any suitable arrangement.

The aerial vehicle can alternatively be any other suitable aerial vehicle. For instance, in other embodiments, the aerial vehicle can be an aerial vehicle of any suitable category, class, or type, and in examples can be one or more of: a fixed-wing aircraft, a gyrocraft (e.g., autogyro), a single engine aerial vehicle, a multi-engine aerial vehicle, a hybrid aerial vehicle including fixed-wing and rotor components, an aerial vehicle with turbine components, an aerial vehicle without a power plant (e.g., a glider), a multi-terrain functional aerial vehicle (e.g., a seaplane, an amphibious aerial vehicle, an aerial vehicle with skis, etc.), and any other suitable vehicle.

As such, in relation to coupling regions between the aerial vehicle and the systems described herein, the aerial vehicle can have any suitable form factor for fuselage and/or airframe components, as described in further detail below.

1.1 Ballistic Subsystem.

The ballistic subsystem 110 functions to affect one or more of the orientation, position, velocity vector, and acceleration (PVA) of the aerial vehicle. The rockets 115 of the ballistic subsystem 110 are preferably a plurality of rocket engines (e.g., defining one or more rocket engine arrays), but can additionally or alternatively include only a single rocket engine and/or include any other suitable rocket elements. The rocket engines are preferably configured to remain attached to and exert force upon the aerial system during rocket engine firing, but the ballistic subsystem 110 can additionally or alternatively include rockets that detach from the aerial system during firing, and/or include rocket elements configured in any other suitable manner.

In some circumstances, if the aerial vehicle (or a subsystem thereof, such as the rotor) experiences power loss (e.g., complete power loss, partial power loss, etc.; such as resulting from power plant failure) and/or another catastrophic failure (e.g., mid-air collision), the ballistic subsystem 110 can fire one or more rockets of its array of rockets (e.g., retrorockets, any other suitable rockets) to reorient and/or decelerate the aerial vehicle prior to impacting the ground or another object. As such, in relation to orientation, the ballistic subsystem can fire one or more rockets with suitable thrust components (e.g., amplitude and direction) to affect the pitch, yaw, and/or roll of the aerial vehicle. In relation to PVA, the ballistic subsystem can fire one or more rockets with suitable thrust components (e.g., amplitude and direction) to affect: position of the aerial vehicle in space (e.g., 2D space, 3D space), velocity of the aerial vehicle (e.g., velocity vector amplitude, velocity vector direction, etc.), and/or acceleration of the aerial vehicle (e.g., acceleration amplitude, acceleration vector direction, change in acceleration over time, etc.). In specific examples, the ballistic subsystem 110 can be used to lift the aerial vehicle to an appropriate altitude for parachute deployment, prior to impact, in relation to the deployable parachute subsystem 130 described below. Additionally or alternatively, the ballistic subsystem 110 can reposition and/or change energy state of the aerial vehicle prior to impact in any other suitable manner.

As shown in FIG. 1, the set of rockets 115 of the ballistic subsystem 110 can be configured in an array and coupled as a unit to the airframe or fuselage of the aerial vehicle. As described in relation to the mounting unit 120 below, the array can be configured to couple, by way of the mounting unit 120, to the aerial vehicle, wherein forces caused by the rockets are directed, at least partially, through the mounting unit 120 as a structural component of the aerial vehicle. In variations wherein the set of rockets 115 is configured in an array, the array can be a rectangular array, a polygonal array, an ellipsoid array, a circular array, an array following a surface morphology of the fuselage of the aerial vehicle, an amorphous array, and/or any other suitable type of array.

Figure 2:
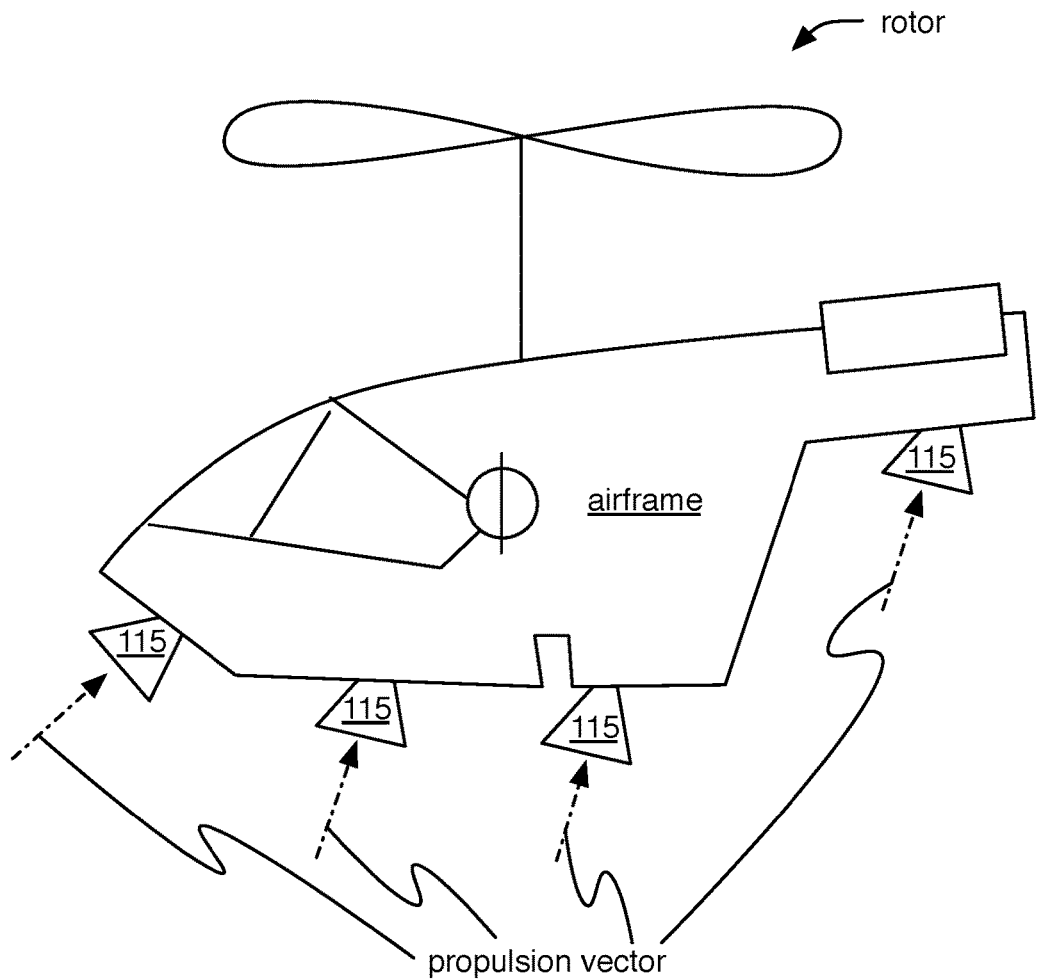
FIG. 2 is a schematic representation of a variation of a portion of a safety system.

Additionally or alternatively, as shown in FIG. 2, one or more of the set of rockets 115 of the ballistic subsystem 110 can be individually positioned at one or more regions of the aerial vehicle. As such, in these variations, individual rockets of the set of rockets 115 can be configured to provide thrust in a manner that applies forces to specific individual regions of the aerial vehicle. In variations wherein the aerial vehicle comprises separate portions (e.g., a cockpit region, an instrument region, a sensor region, control surface regions, etc.), each of the set of rockets 115 can be coupled to a corresponding separate portion of the aerial vehicle. In one example, involving coupling between individual rockets and portions of the aerial vehicle, one or more of the set of rockets 115 can be operable to separate and propel components of the aerial vehicle in different directions. In one specific application, a subset of the set of rockets can be operable to separate and jettison compromised portions of the aerial vehicle (e.g., compartments of the aerial vehicle with inextinguishable flames) that are not required for landing safely, while one or more other subsets of the set of rockets can be operable to cushion any impact of other portions of the aerial vehicle (e.g., portions containing passengers, portions containing cargo, etc.) by reducing kinetic energy of the damaged aerial vehicle prior to impact (e.g., by firing downward as the aerial vehicle approaches the ground, thereby reducing the aerial vehicle's downward velocity at impact).

The rockets are preferably arranged below a horizontal midplane of the aerial system (e.g., plane including a central reference point, such as the aerial system center of gravity; plane normal a vertical reference axis, such as a rotor axis, axis normal the ground and/or parallel a gravity vector when the aerial system is in a landed configuration fully supported by the ground, etc.), such as being arranged in, on, and/or below a belly of the airframe. For example, in a rotorcraft including a main rotor above the airframe, the rockets can oppose the main rotor across the horizontal midplane. However, any or all of the rockets can alternatively be arranged on and/or above the horizontal midplane.

However, the set of rockets 115 of the ballistic subsystem 110 can alternatively be configured in any other suitable manner.

The set of rockets 115 can include any suitable number of rockets (e.g., 1-10, 10-30, 30-50, 50-100, more than 100, etc.), and in specific examples, can include between 10 and 30 rockets arranged as a cluster and/or coupled to different regions of the aerial vehicle. The rockets can use any suitable propellant type (e.g., solid, liquid, gas, gel, etc.) and propellant quantity to provide suitable thrust characteristics and duration for reducing kinetic energy of the damaged aerial vehicle prior to impact and/or for any other suitable application involving safety of the aerial vehicle. One or more of the rockets can optionally be controlled (e.g., throttled) within a range of possible firing intensities (e.g., corresponding to different fuel burn rates); however, all or some of the rockets can alternatively be operable only between an on state and an off state. Each of the set of rockets 115 can be a single-use rocket that is no longer useable after its propellant source is depleted; alternatively one or more of the set of rockets 115 can be a multi-use rocket that can be re-used (e.g., following replenishment of its propellant). Still alternatively, one or more of the set of rockets 115 can share a propellant source.

The rocket motors are preferably oriented such that each rocket propulsion vector (e.g., representing a force exerted on the airframe by the rocket motor) and/or a net propulsion vector (e.g., associated with the set of all rocket motors or any suitable subset thereof) includes an upward component (e.g., oriented away from the ground when the aerial system is in a landed configuration fully supported by the ground; example shown in FIG. 2), such as the vector being within a threshold angle of a vertical axis (e.g., substantially parallel, within 1°, 5°, 10°, 15°, 30°, 45°, 1-5°, 5-20°, 20-60°, etc.). Preferably, a dot product of a propulsion vector (e.g., individual rocket engine propulsion vector, net propulsion vector, etc.) and an upward reference vector (e.g., internal reference, such as a rotor vector directed along the rotor axis from the airframe or midplane to the rotor; external reference, such as a vector opposite the gravity vector or a ground-normal vector directed from the ground into the air; etc.) is greater than zero. However, any or all of the rocket motors can alternatively include downward components, be substantially lateral (e.g., include only an insignificant vertical component), and/or have any other suitable orientation.

The rocket motors of the set of rockets 115 can be fixed to one or more of the fuselage or the airframe of the aerial vehicle, such that the rockets of the set of rockets 115 are fixed in orientation relative to the aerial vehicle. In variations of this configuration, activation of different combinations of the set of rockets 115 can produce any net force vector with any suitable force magnitude and/or orientation (e.g., within a range of net force vectors achievable by the system, selected from a discrete set of achievable net force vectors, etc.), in order to affect motion of the aerial vehicle. Additionally or alternatively, one or more of the rockets can include a thrust vectoring module (e.g., gimbaled rocket engine and/or nozzle, exhaust vanes, fluid injection module, etc.). For example, motors of one or more of the set of rockets 115 can be gimbaled to the fuselage or airframe, such that the orientation(s) of one or more of the set of rockets 115 can be independently adjustable relative to the aerial vehicle. In variations of this configuration, the gimbal(s) of the set of rockets 115 can be used to dynamically control the force vector produced by the set of rockets 115 by changing relative angles between one or more rockets and the fuselage of the aerial vehicle. In variations wherein the motors are actuatable, actuation can be controlled with electrical signals (e.g., in a manner analogous to using full authority digital control systems), by mechanical subsystems for rocket motor actuation, and/or in any other suitable manner. Furthermore, using either or combinations of both configurations, real time control of a trajectory of the aerial vehicle can be achieved by modulating one or more of: rocket force output, which subset of the set of rockets is activated, and orientation of rockets of the set of rockets.

The rockets can additionally or alternatively include one or more rocket motors arranged on (e.g., affixed to) one or more rotor blades of the aerial system rotor (e.g., oriented substantially tangentially, such as with propulsion vectors substantially normal the rotor axis), preferably arranged at or near the rotor blade tips. These rotor blade rockets preferably function to propel the rotor (e.g., increase rotor rotation about the rotor axis), but can additionally or alternatively perform any other suitable functions.

Furthermore, each of the set of rockets 115 is preferably activated using an autonomous system (e.g., control system), as described above, wherein the autonomous system is operable to use aerial vehicle state, orientation, and/or environmental conditions to control activation of one or more of the set of rockets 115. For example, in the event that the aerial vehicle has sustained airframe and/or other structural damage prior to rocket activation, the autonomous system can acquire data from sensors of the aerial vehicle that are indicative of vehicle state, orientation, and environmental conditions, in order to determine which of the set of rockets should be activated, as well as how much thrust and for what duration thrust should be applied from the specific rockets. Additionally or alternatively, in another example, the autonomous system can be configured to apply at least one "test pulse" of thrust from one or more of the set of rockets (e.g., in order to assess changes in weight and balance of the aerial vehicle due to damage, to assess kinematic behavior of the aerial vehicle in current environmental conditions, etc.). However, automation of activation of the set of rockets can additionally or alternatively be implemented in any other suitable manner.

The ballistic subsystem 110 with its set of rockets 115 preferably includes a "dead man's switch" configuration, such that the ballistic subsystem 110 engages even if all other systems of the aerial vehicle are incapacitated. For example, in response to determining that other systems of the aerial vehicle (e.g., all other systems; relevant control systems, such as systems responsible for controlling the ballistic subsystem to activate; etc.) are incapacitated (e.g., based on loss of connectivity to the system instantaneously or for greater than a threshold period of time, such as 10 ms, 30 ms, 100 ms, 300 ms, 1 s, 3 s, 10 s, 30 s, 100 s, 1-1000 ms, 1-1000 s, etc.; based on sensor measurements indicative of damage to and/or destruction of the system; etc.). The ballistic subsystem 110 can additionally or alternatively be configured to engage in response to receiving an emergency input (e.g., from an operator or passenger of the aerial system), such as in response to detecting actuation of an emergency conditions input (e.g., switch, button, etc.). However, the ballistic subsystem 110 can alternatively be configured in any other suitable manner.

The mounting unit 120 couples the ballistic subsystem 110 to the aerial vehicle, and functions to provide robust coupling between the set of rockets of the ballistic subsystem and the aerial vehicle. Additionally or alternatively, the mounting unit 120 can provide releasable coupling between the ballistic subsystem 110 and the aerial vehicle, in situations where the option to reduce gross weight of the aerial vehicle is preferred, after the vehicle is on a safer trajectory by the ballistic subsystem.

The mounting unit 120 can couple to a main structural support component of the airframe or fuselage of the aerial vehicle. Additionally or alternatively, the mounting unit 120 can include one or more robust components of the ballistic subsystem 110. In one such variation, rocket tubes of the set of rockets, due to their wall thickness and material composition, can be used as a structural support feature of the aerial vehicle. In a specific example, the engine mount (e.g., mounting the power plant to the aerial vehicle) of the aerial vehicle can be directly coupled to the cluster of the set of rockets or the mounting unit 120 of the set of rockets 115. In other examples, other components of the aerial vehicle can thus be mounted to rocket tubes or other regions of the set of rockets 115.

In variations of the system 100 comprising the mounting unit 120, the mounting unit 120 can have a position that is laterally centered about the center of gravity (CG) of the aerial vehicle (e.g., the CG of the aerial vehicle with or without the mounting unit; the CG of the aerial vehicle alone, the known or anticipated CG of the aerial vehicle including contents such as passengers and/or removable equipment, etc.). The position of the mounting unit 120 can have a position that is slightly forward of the CG; however, the mounting unit 120 can alternatively have any other suitable position forward or aft of the CG of the aerial vehicle. Still alternatively, the mounting unit 120 can have any other suitable position relative to the CG of the aerial vehicle (laterally, or forward/aft). In variations wherein the set of rockets 115 includes rockets distributed at different regions of the aerial vehicle, the system 100 can include a set of mounting units operable to couple each rocket to the aerial vehicle (e.g., a separate mounting unit for each rocket engine, a separate mounting unit for each region in which rocket engines are mounted, etc.).

In a specific example, the ballistic subsystem 110 can comprise an array of rockets coupled to a rotorcraft (e.g., Mosquito model rotorcraft manufactured by Innovator Technologies) by a mounting unit 120 coupled to the belly of the rotorcraft. The mounting unit 120 can be laterally centered and slightly forward of the CG. However, the ballistic subsystem 110 can alternatively be coupled to any other suitable aerial vehicle and/or be configured in any other suitable manner, as described above.

The ballistic subsystem 110 can, however, be configured in any other suitable manner.

1.2 Parachute Subsystem.

In some variations, the system 100 can further include a deployable parachute subsystem 130 coupled to a region of the aerial vehicle and operable to deploy a parachute 135 (e.g., as shown in FIG. 1). The deployable parachute subsystem 130 functions to provide a drag increasing option that reduces kinetic energy of the aerial vehicle, adjusts the trajectory of the aerial vehicle (e.g., to less hazardous landing sites), and/or adjusts the orientation of the aerial vehicle (e.g., to decrease anticipated impact damage to the aircraft and/or contents, to enable and/or enhance use of other safety system elements such as the ballistic subsystem, etc.) prior to impact.

The parachute 135 (e.g., parachute canopy) of the deployable parachute subsystem 130 can be radially symmetric (e.g., with a circular footprint), or can alternatively be non-radially symmetric. Still alternatively, the parachute 135 of the deployable parachute subsystem 130 can have a lateral or longitudinal axis of symmetry (e.g., as in a ram-air parachute and/or other wing-shaped parachute, such as a rectangular or tapered canopy), such that the parachute 135 can be steerable relative to winds aloft. The parachute 135 is preferably composed of a synthetic material that is resistant to moisture, puncture, and/or UV damage; however, the parachute 135 can alternatively be composed of any other suitable material. The deployable parachute subsystem 130 can optionally include one or more pilot chutes (e.g., a pilot chute coupled to each parachute 135). The deployable parachute subsystem 130 can additionally or alternatively comprise any suitable number of parachutes.

The deployable parachute subsystem 130 can be operable to deploy the parachute 135 using passing airflow, after releasing a portion of the parachute 135 in a manner that interacts with relative wind and the aerial vehicle. Additionally or alternatively, the deployable parachute subsystem 130 can include electrical and/or mechanical means for parachute deployment. In one such variation, the deployable parachute subsystem 130 can comprise one or more rockets, such as rockets that propel the parachute from the aerial vehicle using electrical signals (e.g., in a manner analogous to using full authority digital control systems) and/or by mechanical subsystems for rocket activation.

Figure 3:
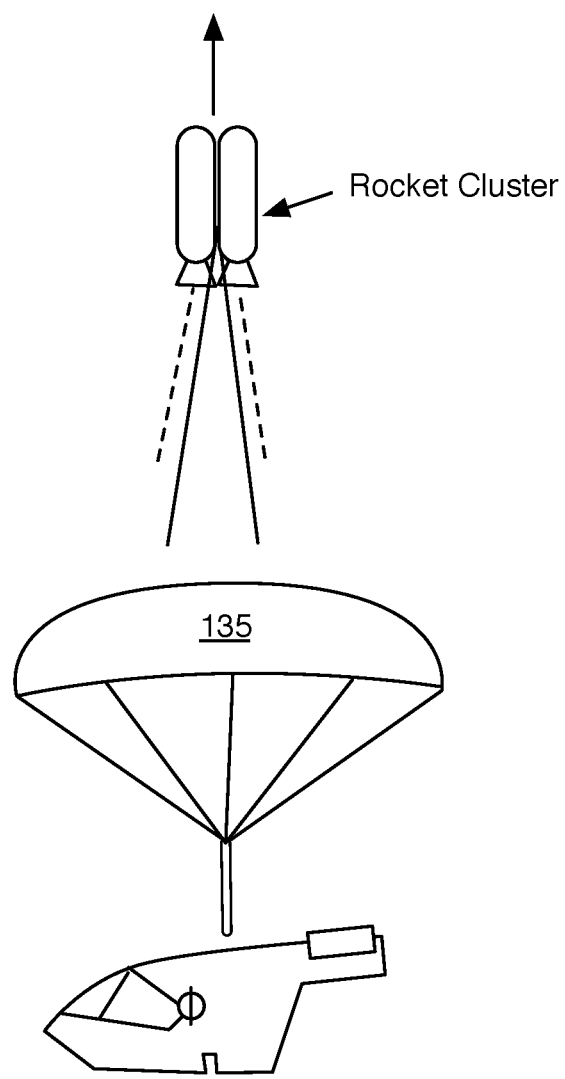
FIG. 3 is a schematic representation of a variation of a portion of a safety system for an aerial vehicle.

In variations wherein the parachute 135 is deployed, at least in part, using one or more rockets, the rocket(s) can be directly mounted to the parachute 135, or can alternatively be tethered (or otherwise connected) to the parachute 135 (e.g., as shown in FIG. 3), such that activation of the rocket leads the parachute 135 along a trajectory and/or a sustained position relative to aerial vehicle, thereby pulling the parachute 135 in tow. Use of a tethering system can thus promote proper deployment in a manner that promotes reliable opening of the parachute 135. In some embodiments, the connector (e.g., tether) is sufficiently long that the parachute does not substantially affect airflow near the aerial system (e.g., near the rotor, such as airflow driving and/or driven by the rotor); however, the parachute subsystem can additionally or alternatively include a connector of any suitable length, and/or can couple the parachute to the other elements of the aerial system in any other suitable manner. Additionally or alternatively, an autonomous system associated with systems of the aerial vehicle can be used to govern a trajectory of the parachute, by way of the rocket(s), based upon one or more of: present trajectory of the aerial vehicle, predicted trajectory of the aerial vehicle, wind factors (at altitudes along trajectory), structural integrity of the aerial vehicle, capabilities of the aerial vehicle propulsion system, and any other suitable factor. However, the parachute 135 can be deployed from the aerial vehicle 135 in any other suitable manner.

Similar to operations described in relation to the ballistic subsystem 110 above, rockets coupled to the parachute 135 (e.g., by direct mounting, by tethering, etc.) can be used to lift the aerial vehicle to an appropriate altitude (e.g., in promoting parachute deployment) prior to impact, such that the parachute 135 has adequate altitude and/or time to appropriately reduce the kinetic energy of the aerial vehicle prior to impact. In one such variation, once a tether coupled to the parachute 135 is fully extended, rocket forces directly exerted on the parachute 135 and the aerial vehicle can be used to: reduce and/or increase the velocity (e.g., downward velocity component, upward velocity component, one or more lateral velocity components, overall velocity, etc.) of the aerial vehicle rapidly and/or increase the altitude of the aerial vehicle such that the parachute 135 can fully inflate and provide sufficient drag to bring the aerial vehicle down safely. In specific examples, the rocket forces can be used to: decrease aerial vehicle downward velocity (e.g., prior to ground impact, such as immediately prior to landing; working in concert with and/or independently from the parachute), increase aerial vehicle upward velocity, change aerial vehicle vertical velocity from downward to upward, increase aerial vehicle lateral velocity, decrease aerial vehicle lateral velocity, change aerial vehicle lateral velocity direction, and/or change aerial vehicle velocity in any other suitable manner. Additionally or alternatively, the parachute 135 and/or rockets associated with (e.g., attached to, such as tethered to or attached directly to) the parachute can reposition, reorient, and/or change energy state of the aerial vehicle prior to impact in any other suitable manner.

Additionally or alternatively (e.g., in variations wherein the deployable parachute subsystem 130 is actively deployed), the deployable parachute subsystem 130 can include a "dead man's switch" configuration (e.g., as described above regarding a "dead man's switch" of the ballistic subsystem; a single "dead man's switch" shared by the parachute subsystem and ballistic subsystem, identical or similar to but independent of the ballistic subsystem "dead man's switch", different than the ballistic subsystem "dead man's switch", etc.), such that the deployable parachute subsystem 130 engages even if all other systems of the aerial vehicle are incapacitated. However, the deployable parachute subsystem 130 can alternatively be configured in any other suitable manner.

Figure 4A:
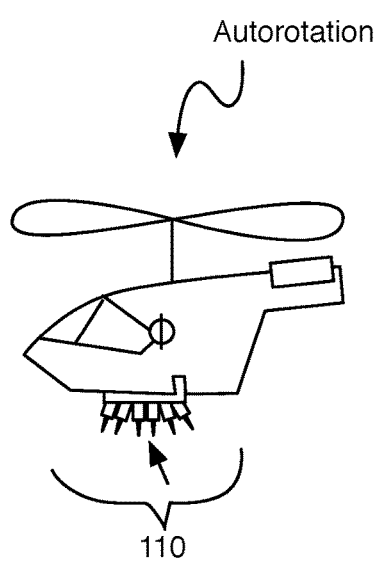
FIGS. 4A and 4B depict variations of applications implementing a safety system for an aerial vehicle.
Figure 4B:
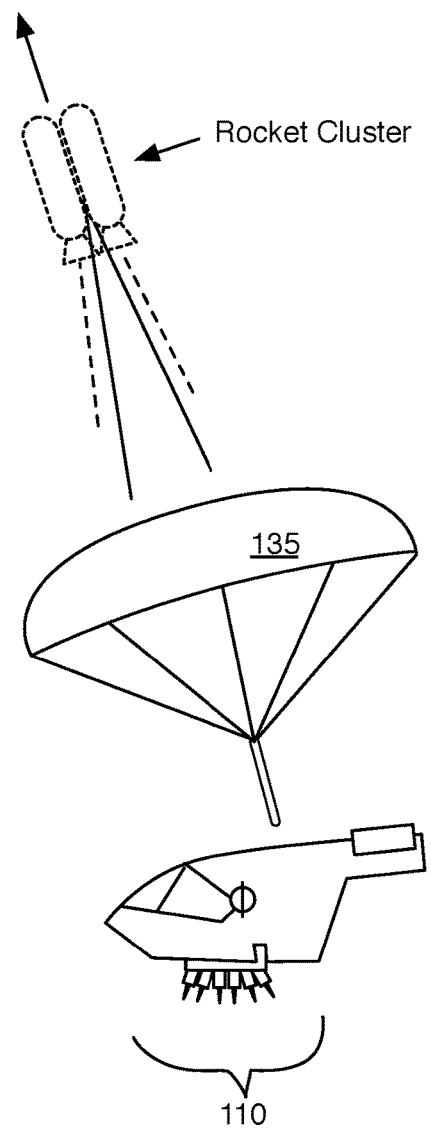

As indicated above, the ballistic subsystem 110 and the deployable parachute subsystem 130 can be activated independently of each other. In one example scenario, where the aerial vehicle is a rotorcraft that has experienced power loss without structural failure or control malfunction, the aerial vehicle can implement (e.g., using the autonomous system), a combination of autorotation and rocket firing from the ballistic subsystem 110, in order to land safely, as shown in FIG. 4A. In another example scenario, where the aerial vehicle is a rotorcraft that has experienced structural failure and/or control malfunction, the aerial vehicle can implement (e.g., using the autonomous system), a combination of parachute deployment and rocket firing from the ballistic subsystem 110, in order to land safely, as shown in FIG. 4B. As such, in these scenarios and other scenarios, activating of one or both the ballistic subsystem 110 and the deployable parachute subsystem 130 can be used to ensure safety at any altitude, attitude, and airspeed, including zero airspeed/zero altitude situations.

The system 100 can include one or more elements for actuator integration redundancy. As such, should one actuator fail to move due to binding, signal loss, or any other failure mechanism, an alternative control affector can be engaged to perform the same function as the failed actuator. The alternative control affector(s) can be placed in parallel with the primary control affector. In a specific example, if a first actuator fails, a breakaway system (e.g., shear pin, giveaway system, etc.) can be used to disengage the first actuator and/or to allow a redundant functioning actuator to overrule the first actuator. In relation to actuator redundancy, should all actuators fail (or in any other suitable circumstances), the system 100 can additionally or alternatively include a configuration for disengagement of the redundant system, thereby allowing a passenger or other entity (e.g., remote operator) to assume control of the aerial vehicle systems. However, the system 100 can alternative omit redundant actuator systems.

1.3 Additional Safety Features.

Figure 6A:
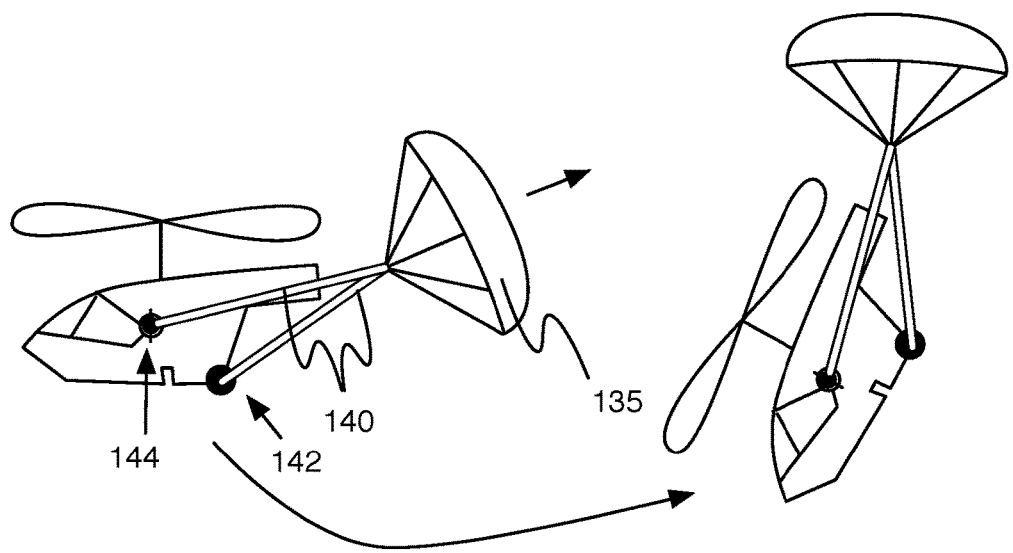
FIGS. 6A and 6B depict alternative variations of a safety system for an aerial vehicle.
Figure 6B:
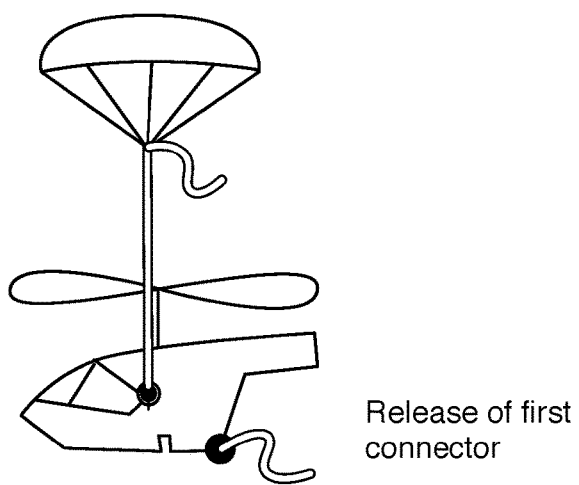

As noted above, the deployable parachute system 130 can additionally or alternatively include a connector 140 coupling the parachute 135 to a first anchoring point 142 of the aerial vehicle. The deployable parachute system 130 can additionally be coupled to a second anchoring point 144 separated from the first anchoring point of the aerial vehicle (or to any other suitable number of additional anchoring points separated from each other). The deployable parachute system can be coupled to both the first and second anchoring points by a single connector element (e.g., a connector element such as a tether running from the parachute 135 to the first anchoring point 142 and then from the first anchoring point 142 to the second anchoring point 144, such as shown in FIGS. 1 and/or 5A), by separate connector elements (e.g., a first connector element such as a first tether running from the parachute 135 to the first anchoring point 142, and a second connector element such as a second tether running from the parachute 135 to the second anchoring point 144, such as shown in FIG. 6A), and/or in any other suitable manner.

Figure 7:
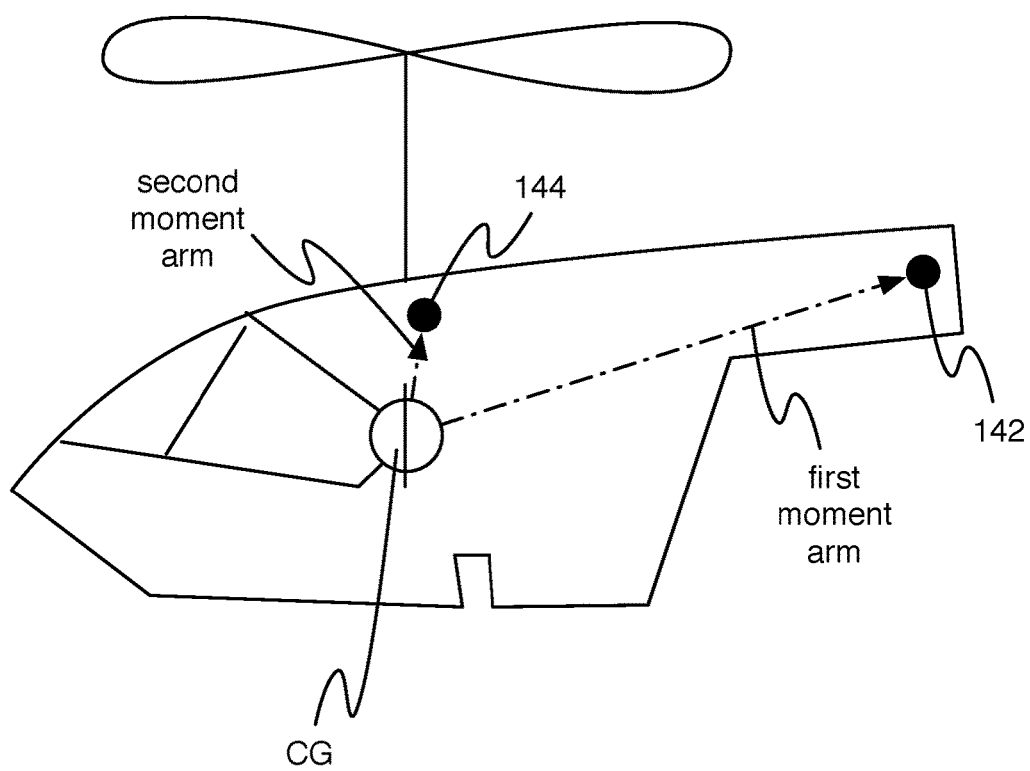
FIG. 7 depicts an embodiment of an aerial vehicle with parachute anchors.

The use of multiple anchoring points (e.g., first and second anchoring point) can result in the deployed parachute exerting different torques (e.g., torques of different direction and/or magnitude) on the aerial system and/or biasing the aerial system toward different orientations (e.g., level, pitched downward, pitched upward, etc.), depending on how the parachute is anchored (e.g., by the first anchoring point, by the second anchoring point, by both anchoring points, etc.). The first and second anchoring points are preferably arranged such that a substantially non-zero angle is defined between the first anchor moment arm (e.g., vector from a reference origin, such as the CG, to the first anchoring point 142) and the second anchor moment arm (e.g., vector from the reference origin to the second anchoring point 144), such as shown in FIG. 7. For example, the angle between the moment vectors can be greater than a minimum threshold angle (e.g., 1°, 5°, 10°, 15°, 30°, 45°, 60°, 80°, 90°, 100°, 120°, 1-15°, 15°-45°, 45-120°, etc.) and/or less than or equal to a maximum threshold angle (e.g., 1°, 5°, 10°, 15°, 30°, 45°, 60°, 80°, 90°, 100°, 120°, 1-15°, 15°-45°, 45-120°, etc.). However, the moment vectors can alternatively define any other suitable angle. In variations, the first anchoring point 142 can be distant from a center of gravity (CG) and/or longitudinal midplane (e.g., plane including a vertical axis, such as the rotor axis, and a pitch axis through the CG) of the aerial vehicle, and the second anchoring point 144 can be closer to the CG and/or vertical midplane of the aerial vehicle (e.g., for a rotorcraft with movable blades). For example, the magnitude of a cross product of the first moment arm with a rotor vector (e.g., directed along the rotor axis from the airframe or horizontal midplane to the rotor) can be greater than the magnitude of a cross product of the second moment arm with the rotor vector (e.g., greater by a threshold amount, such as 10%, 25%, 50%, 100%, 150%, 200%, 250%, 300%, 500%, 1000%, etc.). The connector 140 preferably functions to allow for parachute deployment in a manner that does not adversely interfere with rotors or other moving components of the aerial vehicle. For instance, while a rotor of an aerial vehicle is moving (but not autorotating), forces generated by the rotor can suck a deployed parachute into blades of the rotor in an undesirable manner (e.g., causing entanglement, parachute and/or rotor damage, etc.). Thus, the connector 140 can preferably prevent this scenario and/or other undesirable scenarios.

At least one of the first anchoring point 142 and the second anchoring point 144 of the connector 140 can be releasable, such that one or more regions of the connector 140 (and/or one or more connector elements) can be selectively uncoupled from the aerial vehicle during use of a safety mechanism involving the parachute 135. In a first variation, the first anchoring point 142 can be positioned proximal the region of parachute deployment, preferably such that the parachute is deployed away from moving components of the aerial vehicle and maintained away from the moving components by the first anchoring point 142 (e.g., as shown in FIGS. 1 and/or 5A). In a specific example, the system 100 can thus include a tail-launched parachute with a fixed first anchoring point at a tail-region of a rotorcraft. However, the fixed first anchoring can be configured in any other suitable manner.

Figure 5A:
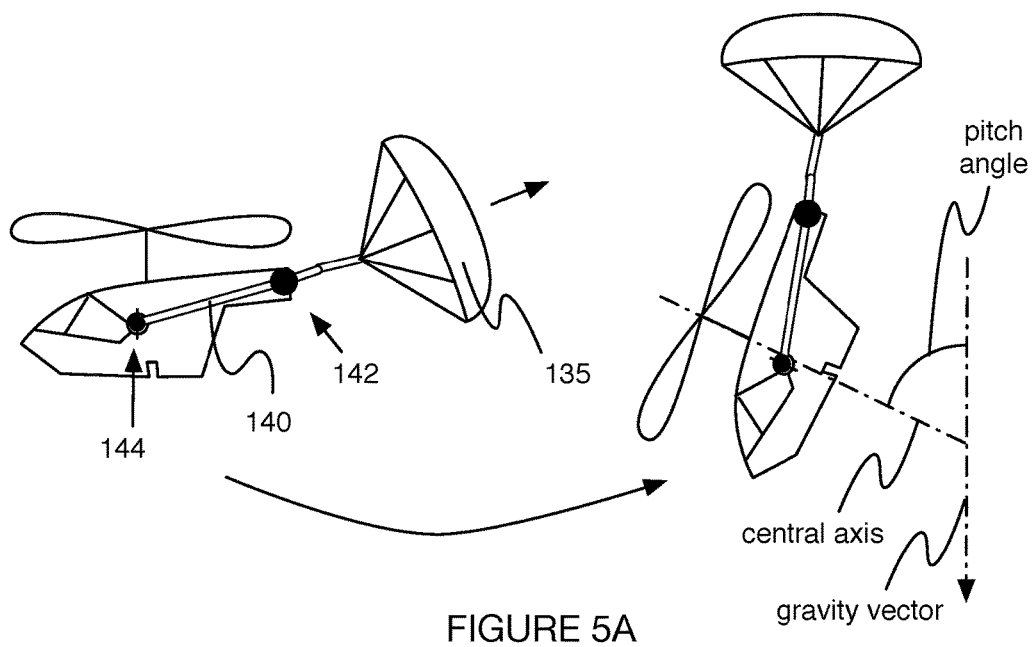
FIGS. 5A and 5B depict variations of a safety system for an aerial vehicle.
Figure 5B:
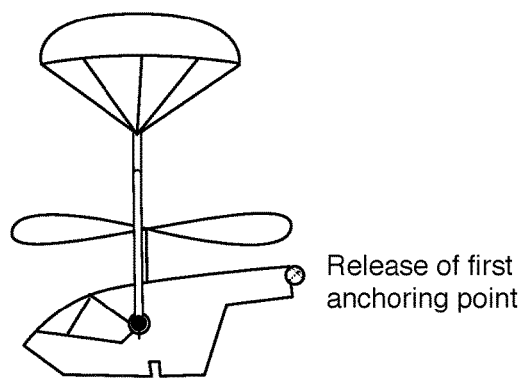

Additionally (e.g., as shown in FIGS. 5B and/or 6B), the first anchoring point 142 (and/or, in variations including multiple connector elements, a connector element coupled to the first anchoring point) can be released, thereby separating the connector 140 from the aerial vehicle at the first anchoring point 142. In examples, the first anchoring point 142 can be released once (e.g., in response to, such as immediately after or a threshold time interval after) oscillations associated with parachute deployment and/or wind effects have been suitably reduced, once the rotor state is acceptable for first anchoring point release (e.g., after rotor rotation speed has fallen below a threshold value), and/or once any other suitable criteria have been met. Additionally or alternatively, release of the first anchoring point 142 can be controlled by the autonomous system described above. The release mechanism can be mechanically driven, hydraulically driven, electrically driven (e.g., electrically-activated explosive release mechanism, piezoelectric release mechanism, etc.), and/or driven in any other suitable manner.

As such, once the first anchoring point 142 has been released, the second anchoring point 144 can be used to reorient the aerial vehicle in space, preferably in a manner that puts occupants of the aerial vehicle approximately upright again (e.g., as shown in FIGS. 5B and/or 6B). However, some variations of the system 100 can alternatively omit release of the first anchoring point 142 (e.g., in variations wherein the cabin containing occupants can rotate within the fuselage to adjust orientation of the occupants in space relative to the aerial vehicle.

Figure 8A:
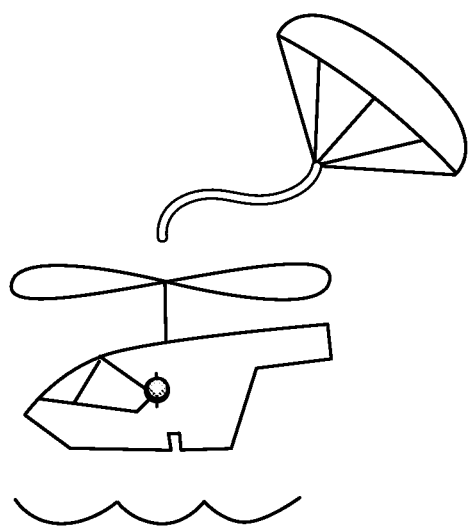
FIGS. 8A and 8B depict specific examples of methods using a safety system for an aerial vehicle.
Figure 8B:
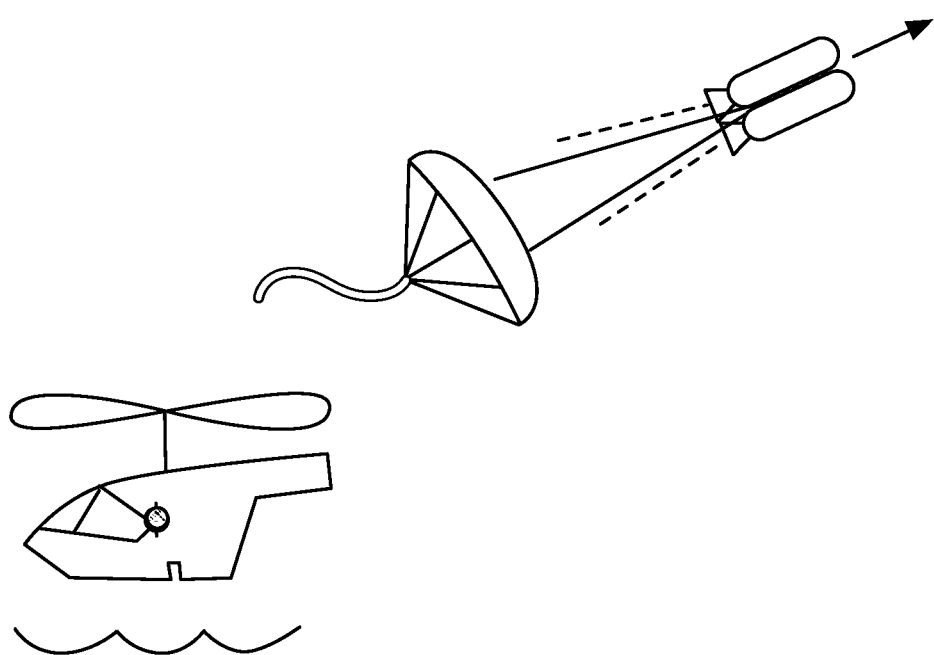

In some variations, as indicated above, the second anchoring point 144 (and/or any other anchoring points) can also be releasable from the aerial vehicle, in order to release the parachute entirely away from the aerial vehicle when desired and/or to promote safety. In one example, release of all anchoring points between the parachute 135 and the aerial vehicle can be used to separate the parachute 135 prior to landing, such that the parachute does not interfere with exit of the occupants from the aerial vehicle. In a more specific example (e.g., as depicted in FIG. 8A), in the event of a forced water landing and/or if a portion of the aerial vehicle is on fire/smoking, the parachute can be entirely released from the aerial vehicle, by the first and second anchoring points 142, 144 once the aerial vehicle has sufficiently slowed down prior to impact. The parachute 135 can thus move away from the aerial vehicle and allow occupants to exit without interference. In relation to this feature, rockets coupled to the parachute can be used to actively deliver the parachute 135 away from the aerial vehicle after the parachute is released, as shown in FIG. 8B, thereby further promoting non-interference with exit of the occupants.

While the first anchoring point 142 is preferably away from the center of gravity and/or moving components of the aerial vehicle, and the second anchoring point 144 is preferably near the center of gravity (e.g., to put occupants upright again), the first and/or the second anchoring points 142, 144 can additionally or alternatively be positioned anywhere else relative to the aerial vehicle.

2. Method.

Figure 9A:
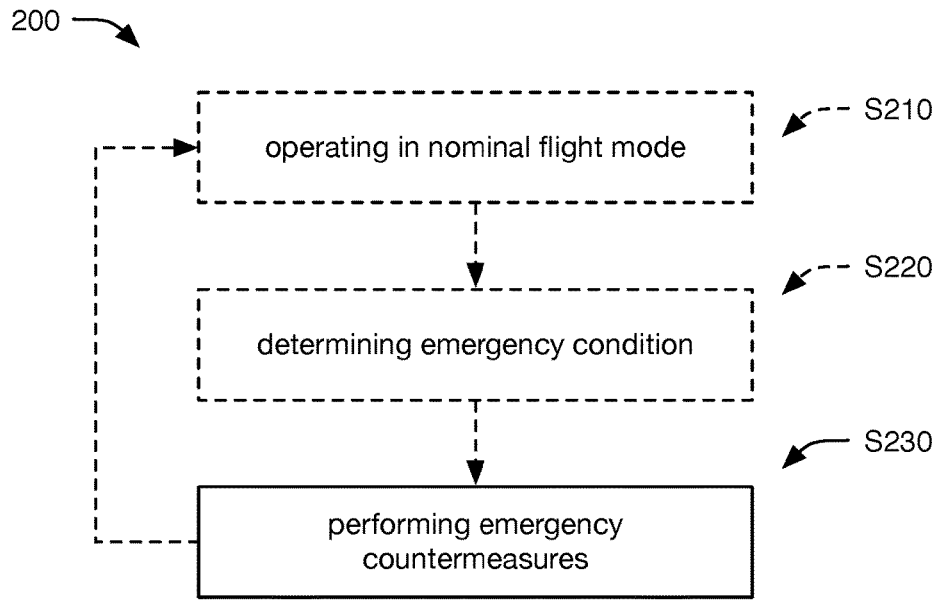
FIG. 9A depicts a flowchart representation of an embodiment of a method of aerial vehicle operation.

A method 200 for aerial system operation preferably includes performing emergency countermeasures S230, and can additionally or alternatively include operating the aerial vehicle in a nominal flight mode S210, determining an emergency condition S220, and/or any other suitable elements (e.g., as shown in FIG. 9A). The method 200 is preferably performed with an aerial vehicle including a safety system 100 (e.g., as described above), but can additionally or alternatively be performed using any other suitable systems.

Operating in a nominal flight mode S210 (e.g., as described in U.S. application Ser. No. 15/661,763, titled "Vehicle System and Method for Providing Services", which is herein incorporated in its entirety by this reference) preferably functions to control the aerial vehicle during normal flight operations. In variations in which the aerial vehicle is a rotorcraft, S210 preferably includes controlling one or more rotors of the rotorcraft to rotate about their respective rotor axes (e.g., controlling a power plant of the rotorcraft to drive rotor rotation).

During performance of S210, the aerial vehicle preferably maintains its orientation within a nominal orientation envelope. For example, the vehicle pitch can take on values within a threshold range from 0 (e.g., no more than a threshold pitch, such as positive and/or negative 10°, 15°, 20°, 25°, 30°, 35°, 40°, 5-20°, 20-60°, etc.) and/or from a nominal pitch value (e.g., 0°; positive or negative 1°, 2°, 3°, 5°, 7.5°, 10°, 12.5°, 15°, 20°, 25°, 30°, 0-3°, 3-15°, 15-45°, etc.). The vehicle pitch is preferably a signed angle (e.g., wherein negative values are downward pitches in which the vehicle front drops downward, and positive values are upward pitches in which the vehicle front rises upward) between projections, onto a longitudinal midplane, of a central axis (e.g., defined by the aerial vehicle) and an external vertical reference (e.g., gravity vector), such as shown in FIG. 5A. The central axis can be a rotor axis, a vehicle vertical reference axis (e.g., when the aerial vehicle is fully supported by the ground, an axis parallel a gravity vector and/or normal the ground supporting the vehicle). The longitudinal midplane preferably includes the CG and is preferably normal a vehicle pitch axis. However, the pitch can alternatively be defined in any other suitable manner.

Determining an emergency condition S220 preferably functions to determine that the aerial vehicle has exited (and/or may exit) nominal flight conditions (e.g., that an off-nominal and/or undesired event has occurred or may occur).

Such events can include collisions (e.g., with terrain, with traffic, etc.), loss and/or degradation of aerial vehicle control, and/or any other suitable events. In specific examples, the emergency conditions can include: power plant failure (e.g., partial or total power loss; at any time, while operating a rotorcraft inside a dangerous region of the altitude-velocity "dead man's" curve, etc.); flight control surface failure (e.g., surface damage and/or destruction, actuator failure, etc.); an aircraft position, orientation, and/or velocity outside a nominal operation envelope (e.g., pitch and/or roll greater than a threshold value, such as 10°, 20°, 25°, 30°, 35°, 40°, 45°, 5-20°, 20-60°, etc.; rapid altitude loss; etc.); dangerous airflow conditions (e.g., vortex ring state); and/or any other suitable conditions.

S220 can be performed based on measurements sampled by aircraft sensors, based on external information (e.g., remote sensor measurements, traffic warnings, etc.) such as information received at the aircraft via radio, and/or any other suitable information. S220 is preferably performed by the aircraft (e.g., by an autonomous aircraft control system; by a human occupant, such as a pilot, crew member, or passenger; etc.). However, S220 can additionally or alternatively be performed by a remote system (e.g., remote operator and/or control center, air traffic controller, etc.) and/or any other suitable entities; wherein the remote system preferably sends an indication of the emergency condition to the aircraft (e.g., via radio transmission) in response to determination.

Figure 9B:
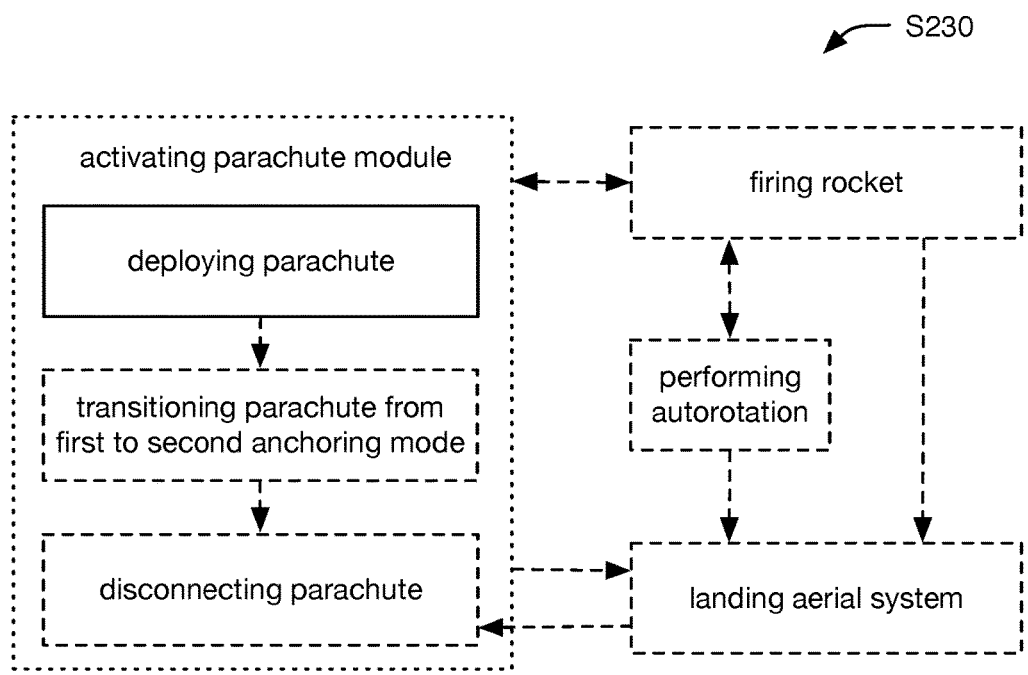
FIG. 9B depicts a flowchart representation of an embodiment of performing emergency countermeasures.

Performing emergency countermeasures S230 preferably functions to recover from and/or compensate for emergency conditions. S230 is preferably performed in response to determining an emergency condition S220 (e.g., immediately in response), but can additionally or alternatively be performed at any other suitable time. S230 can be performed autonomously, by local and/or remote operators (e.g., pilot, crew, passenger, etc.), and/or by any other suitable entities. As shown in FIG. 9B, S230 preferably includes activating one or more aspects of the aerial vehicle safety system (e.g., as described above regarding the safety system 100), such as the deployable parachute subsystem, ballistic subsystem, and/or any other suitable elements of the safety system. S230 can additionally or alternatively include landing the aerial vehicle and/or returning to nominal aerial vehicle operation following resolution of the emergency condition (e.g., as described in U.S. application Ser. No. 15/661,763, titled "Vehicle System and Method for Providing Services", which is herein incorporated in its entirety by this reference).

Activating the deployable parachute subsystem preferably includes deploying the parachute. Deploying the parachute can optionally include propelling the parachute away from the airframe (e.g., using a propellant such as a spring, rocket engine connected to the parachute, etc.). Additionally or alternatively, ambient airflow can be used to deploy the parachute (e.g., wherein the parachute is released from a parachute storage element, thereby allowing ambient airflow to unfurl the parachute and/or carry the parachute away from the airframe).

In variations that include multiple parachute anchoring modes (e.g., as described above regarding multiple anchoring points), the parachute is preferably deployed into a first anchoring mode, wherein the parachute exerts force and/or torque on the airframe with a first moment arm (e.g., at a first anchor point), thereby causing the aircraft to assume a first anchoring mode orientation (e.g., for a tail-mounted first anchor, facing substantially downward, such as shown in FIGS. 5A and/or 6A; for a forward-mounted first anchor, facing substantially upward). In this orientation, the aerial vehicle pitch (and/or difference in pitch from a nominal pitch) is preferably greater than a threshold value (e.g., 10°, 15°, 17.5°, 20°, 22.5°, 25°, 27.5°, 30°, 35°, 40°, 45°, 5-20°, 20-60°, etc.), but can alternatively be any suitable pitch. Such a pitch can function to prevent entanglement of the parachute and/or parachute connector with the rotor (e.g., while the rotor is spinning at high speed, such as close to normal operation speed)

In such variations, activating the deployable parachute subsystem preferably includes include transitioning the parachute between anchoring modes (e.g., from the first anchoring mode to a second anchoring mode). The parachute is preferably transitioned in response to determination of a transition trigger (e.g., satisfaction of a parachute safety criterion). For example, the parachute can be transitioned in response to determining that rotor rotation has slowed below a threshold rate (e.g., 1000 rpm, 500 rpm, 200 rpm, 100 rpm, 75 rpm, 50 rpm, 30 rpm, 20 rpm, 0-10 rpm, 10-50 rpm, 50-250 rpm, etc.), preferably such that the risk of rotor interference with the parachute module (e.g., by causing airflow to pull the parachute into the rotor) is sufficiently low.

Transitioning the parachute between anchoring modes (e.g., into the second mode) preferably includes releasing the connection between the first anchor (or set of anchors) and the parachute. Following release of the connection, the parachute exerts force and/or torque on the airframe with a second moment arm (e.g., at a second anchor point), thereby causing the aircraft to assume a second anchoring mode orientation (e.g., preferably a substantially level orientation, such as shown in FIGS. 5B and/or 6B). In this orientation, the aerial vehicle pitch (and/or difference in pitch from a nominal pitch) is preferably less than a threshold value (e.g., 0°, 1°, 2°, 3°, 5°, 7.5°, 10°, 15°, 17.50, 20°, 22.5°, 25°, 27.5°, 30°, 35°, 40°, 45°, 5-20°, 20-60°, etc.), but can alternatively be any suitable pitch. Transitioning to the second anchoring mode orientation can function to increase occupant comfort and/or ease of egress following vehicle landing (e.g., wherein occupants are returned to a substantially upright orientation in the second anchoring mode), increase landing safety (e.g., enabling a normal landing on aircraft wheels and/or skids), and/or have any other suitable function.

Activating the deployable parachute subsystem can additionally or alternatively include decoupling (e.g., disconnecting) the parachute from the airframe. For example, the parachute can be decoupled in response to aerial vehicle landing and/or soon before landing, in response to parachute entanglement, and/or at any other suitable time. Decoupling the parachute preferably includes disconnecting any parachute anchors that are still connected to the parachute connector (e.g., the second anchor), and can optionally include propelling the parachute away from the airframe (e.g., using a rocket engine coupled to the parachute, such as shown in FIG. 8B). However, activating the deployable parachute subsystem can additionally or alternatively include any other suitable elements performed in any suitable manner.

Activating the ballistic submodule preferably includes exerting a force on the airframe (e.g., by firing one or more of the rocket engines). The force exerted is preferably an upward force (e.g., a force including a component opposing gravity), and can be exerted by firing downward-facing rocket engines (e.g., engines oriented substantially vertically, non-vertical engines generating propulsive force with an upward component, etc.) but can additionally or alternatively include any other suitable forces (e.g., exerted by firing rocket engines with other orientations). Activating the ballistic submodule can function to alter aerial vehicle position, orientation, and/or velocity, preferably to aid or enable safe aerial vehicle landing.

The ballistic submodule can optionally be used to increase the aerial vehicle altitude (e.g., distance above sea level, distance above terrain, etc.), such as to increase available time to effect a safe landing (e.g., if the emergency condition, such as power plant failure, occurs while operating at an airspeed and velocity inside or near the "dead man's" curve). In some embodiments, after increasing aerial vehicle altitude, aerial vehicle descent (and preferably landing) can be controlled by performing an autorotation maneuver, by activating the deployable parachute module, and/or in any other suitable manner. The rocket firing is preferably discontinued (or reduced in intensity, such as to slow descent and/or help control vehicle orientation) during such controlled descent, but can alternatively be sustained and/or controlled at any other suitable intensity. Additionally or alternatively, nominal flight can be resumed (e.g., as described above regarding S210) following ballistic submodule activation (e.g., wherein the additional time allowed by the increased altitude enables recovery of temporarily malfunctioning vehicle systems, such as the power plant).

The ballistic submodule can additionally or alternatively be used to decrease the aerial vehicle downward velocity (e.g., velocity component aligned with gravity). The downward velocity is preferably reduced soon before and/or during the landing process (e.g., wherein the ballistic submodule is used in concert with the parachute and/or rotor, such as in autorotation, to achieve safe landing; wherein the ballistic submodule is used alone to achieve safe landing; etc.), but can additionally or alternatively be reduced at any other suitable time. In a first example, rockets are fired to reduce downward velocity after the parachute has transitioned to the second anchoring mode (e.g., wherein the aerial vehicle has achieved a substantially level orientation). In a second example, rockets are fired to reduce downward velocity after the parachute has been disconnected from the airframe. In a third example, in which the rotorcraft descends using an autorotation maneuver, rockets are fired to reduce downward velocity soon before landing (e.g., within a threshold distance above the ground, such as 10 ft, 25 ft, 40 ft, 50 ft, 60 ft, 75 ft, 100 ft, 150 ft, 200 ft, 10-35 ft, 35-65 ft, 65-100 ft, 100-300 ft, etc.), such as in place of or supplementing the landing flare of a typical autorotation landing maneuver.

The ballistic submodule can additionally or alternatively be used to avoid an imminent collision (e.g., with another aircraft), such as in situations in which the aerial vehicle is functioning nominally (e.g., no power plant and/or control surface malfunctions) but may not be sufficiently maneuverable to avoid the collision (e.g., using traditional flight controls alone). For example, the traditional flight controls (e.g., power plant and/or control surfaces) and the ballistic submodule can be used together (or alternatively, the ballistic submodule can be used alone) to achieve a rapid position and/or velocity change, thereby avoiding the collision (e.g., after which, the aerial vehicle can resume nominal flight, such as described above regarding S210).

Activating the ballistic submodule preferably includes determining the aerial vehicle orientation (e.g., before, during, and/or after rocket engine firing), such as based on aerial vehicle sensors (e.g., accelerometer, gyroscope, magnetometer, camera, radar, etc.). In a first variation, the rocket engines are not used to exert significant upward force on the vehicle (e.g., are not fired at all; are fired only or primarily to effect vehicle orientation changes, such as described below; etc.) until the vehicle is within an acceptable orientation range (e.g., pitch and/or roll within the nominal flight orientation range, within a threshold range of 0, such as within 2°, 5°, 10°, 15°, 17.50, 20°, 22.5°, 25°, 27.5°, 30°, 35°, 40°, 45°, 2-10°, 10-25°, 25-35°, 35-45°, etc.). Activating the ballistic submodule can optionally include altering the aerial vehicle orientation (e.g., to achieve an orientation within the acceptable range, such as a substantially level or upright orientation), such as by using rocket engines (e.g., selectively firing a subset of the engines and/or vectoring the engine thrust, thereby exerting a torque about the CG in order to effect vehicle rotation) and/or flight control surfaces to alter the vehicle orientation. However, vehicle orientation can additionally or alternatively be determined, monitored, and/or altered in any other suitable manner, and the rocket engines can be fired under any other suitable conditions.

S230 can optionally include landing the aerial vehicle (e.g., as described in U.S. application Ser. No. 15/661,763, titled "Vehicle System and Method for Providing Services", which is herein incorporated in its entirety by this reference). The vehicle can be landed using typical flight controls (e.g., using unpowered and/or underpowered maneuvers, such as autorotation and/or gliding; using powered maneuvers; etc.), landed using one or more aspects of the safety system (e.g., rocket engines, parachute, etc.), such as described above, and/or landed in any other suitable manner. The aerial vehicle is preferably landed as soon as practical following determination of the emergency condition and/or activation of the safety system aspect(s), such as performing a safe landing maneuver as soon as possible and/or performing a landing maneuver in the safest practical manner (or in a manner for which the risk of damage, such as damage to the aircraft, occupants, and/or surroundings, is less than a safety threshold). However, the aerial vehicle can alternatively be landed with any other suitable timing.

Alternatively (e.g., wherein normal aerial vehicle system functions are regained), following S230, the aerial vehicle can resume nominal flight operation (e.g., as described above regarding S210) and/or operation in any other suitable flight mode.

However, the method 200 can additionally or alternatively include any other suitable elements performed in any suitable manner.

The methods and/or systems of the invention can be embodied and/or implemented at least in part in the cloud and/or as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A rotorcraft comprising:
    an airframe;
    a rotor rotationally coupled to the airframe about a rotor axis; and
    a parachute module comprising:
        a parachute;
        an anchor submodule comprising a first anchor connected to the airframe at a first point and a second anchor connected to the airframe at a second point; and
        a parachute connector mechanically coupling the parachute to the anchor submodule;
    wherein the first anchor is operable to transition from an anchoring mode to a released mode, wherein:
        in the anchoring mode, the parachute connector is connected to the first anchor and a parachute force is exerted on the first anchor by the parachute connector; and
        in the released mode, the parachute connector is disconnected from the first anchor and connected to the second anchor.

2. The rotorcraft of claim 1, wherein the parachute module further comprises a parachute rocket engine coupled to the parachute and configured to propel the parachute away from the airframe.

3. The rotorcraft of claim 1, wherein:
    the parachute connector comprises a tether defining a first end connected to the parachute and a second end connected to the second anchor; and
    in the anchoring mode, the first anchor is connected to the parachute connector between the first and second ends.

4. The rotorcraft of claim 1, wherein:
    the rotorcraft defines:
        a center of gravity (CG);
        a rotor vector directed along the rotor axis from the airframe to the rotor;
        a first moment arm from the CG to the first point; and
        a second moment arm from the CG to the second point; and
    the magnitude of a first cross product of the rotor vector and the first moment arm is greater than the magnitude of a second cross product of the rotor vector and the second moment arm.

5. The rotorcraft of claim 4, further comprising a rocket engine mechanically connected to the airframe, wherein:
    the rocket engine defines a propulsion vector; and
    a dot product of the propulsion vector and the second moment arm is greater than zero.

6. The rotorcraft of claim 1, further comprising a second rotor rotationally coupled to the airframe about a second rotor axis, wherein:
    the first point is closer to the second rotor axis than to the CG; and
    the second point is closer to the CG than to the second rotor axis.

7. The rotorcraft of claim 6, wherein the first point is distal the CG from the second rotor axis.

8. The rotorcraft of claim 7, wherein the second rotor axis is substantially perpendicular the rotor axis.

9. The rotorcraft of claim 1, further comprising a rocket engine mechanically connected to the airframe.

10. The rotorcraft of claim 9, wherein:
    the rotorcraft defines:
        a center of gravity (CG); and
        a midplane normal the rotor axis, the midplane comprising the CG; and
    the rocket engine opposes the rotor across the midplane.

11. A method for rotorcraft operation, comprising:
    at a rotorcraft comprising an airframe, a rotor rotationally coupled to the airframe about a rotor axis, and a parachute mechanically coupled to the airframe: operating the rotorcraft in a nominal flight mode, comprising controlling the rotor to rotate about the rotor axis;
    after operating the rotorcraft in the nominal flight mode, determining an emergency condition associated with the rotorcraft; and
    in response to determining the emergency condition, at the rotorcraft, performing emergency countermeasures, comprising:
        deploying the parachute in a first parachute anchoring mode, wherein the parachute exerts, on the airframe, a first force with a first moment arm defined from a center of gravity (CG) of the rotorcraft;
        after deploying the parachute, determining a parachute mode transition trigger;
        in response to determining the parachute mode transition trigger, controlling the parachute to transition from the first parachute anchoring mode to a second parachute anchoring mode, wherein the parachute exerts, on the airframe, a second force with a second moment arm defined from the CG; and
        after controlling the parachute to transition from the first parachute anchoring mode to the second parachute anchoring mode, landing the rotorcraft.

12. The method of claim 11, wherein:
    operating the rotorcraft in the nominal flight mode comprises controlling the rotor to rotate about the rotor axis at a first speed greater than a threshold speed; and
    determining the parachute mode transition trigger comprises sampling sensor data indicative of rotor rotation about the rotor axis at a second speed less than the threshold speed.

13. The method of claim 11, wherein:
    the rotorcraft further comprises a first anchor connected to the airframe at a first point, a second anchor connected to the airframe at a second point, and a parachute connector;
    in the first parachute anchoring mode, the parachute connector connects the parachute to the first anchor;
    in the second parachute anchoring mode, the parachute connector connects the parachute to the second anchor; and
    controlling the parachute to transition from the first parachute anchoring mode to the second parachute anchoring mode comprises disconnecting the first anchor from the parachute connector.

14. The method of claim 11, wherein:
    controlling the rotor to rotate about the rotor axis comprises controlling a powerplant of the rotorcraft to drive rotation of the rotor; and
    determining the emergency condition comprises sampling sensor data indicative of failure of the powerplant.

15. The method of claim 11, wherein:
    the rotorcraft further comprises a rocket engine mechanically coupled to the parachute; and
    the method further comprises, after controlling the parachute to transition from the first parachute anchoring mode to the second parachute anchoring mode:
        disconnecting the parachute from the airframe; and
        firing the rocket engine to propel the parachute away from the airframe.

16. The method of claim 11, wherein:
- while operating the rotorcraft in the nominal flight mode, the rotorcraft orientation defines a nominal pitch;
- while in the first parachute anchoring mode, the rotorcraft orientation defines a first mode pitch, wherein the difference between the nominal pitch and the first mode pitch is greater than a threshold angle; and
- while in the second parachute anchoring mode, the rotorcraft orientation defines a second mode pitch, wherein the difference between the nominal pitch and the second mode pitch is less than the threshold angle.

17. The method of claim 16, wherein:
- the threshold angle is greater than 45°; and
- the difference between the nominal pitch and the second mode pitch is less than 15°.

18. The method of claim 11, wherein performing emergency countermeasures further comprises, at a rocket engine mechanically connected to the airframe, exerting a rocket force on the airframe, wherein the rocket force is oriented upward relative to a gravity vector.

19. The method of claim 18, wherein exerting the rocket force comprises, before deploying the parachute, firing the rocket engine.

20. The method of claim 18, wherein exerting the rocket force comprises, after controlling the parachute to transition from the first parachute anchoring mode to the second parachute anchoring mode and before landing the rotorcraft, firing the rocket engine.

* * * * *